US00PP09134P

United States Patent [19]

Enthoven

[11] Patent Number: Plant 9,134

[45] Date of Patent: May 9, 1995

[54] GERANIUM PLANT NAMED MERILOU

[75] Inventor: Adrianus W. M. Enthoven, Wateringen, Netherlands

[73] Assignee: Enthoven Breeding B.V., Wateringen, Netherlands

[21] Appl. No.: 197,346

[22] Filed: Feb. 26, 1994

[51] Int. Cl.[6] ..... A01H 5/00
[52] U.S. Cl. ..... Plt./87.12
[58] Field of Search ..... Plt. 87.12

[56] References Cited

U.S. PATENT DOCUMENTS

P.P. 5,373 12/1984 Schumann ..... Plt./87.12
P.P. 6,717 4/1989 Duemonen ..... Plt./87.12
P.P. 7,930 8/1992 Hanes ..... Plt./87.12

*Primary Examiner*—James R. Feyrer
*Attorney, Agent, or Firm*—Foley & Lardner

[57] ABSTRACT

A new and distinct cultivar of geranium named Merilow, particularly characterized by the combined features of semi-double flowers that are pale lilac in color with a white zone at the base of the upper petals and pale lilac spot that is stronger on the lower petals; average flowering that is equal; compact growth habit with the plant growing rather wide; green foliage with a light zone on the upper side; leaf margins that are slightly incised, double crenated and wavy; short flower stalks that grow above the plant; a large inflorescence with many flowers that open at the same time; and numerous flower buds that are elliptic in shape.

3 Drawing Sheets

The present invention comprises a new and distinct cultivar of geranium, botanically known as *Pelargonium zonale,* and hereinafter referred to by the cultivar name Merilou.

Merilou is a product of a planned breeding program which had the objective of creating new geranium cultivars with semi-double flower form, compact habit, fast rooting, good tolerance to Botrytis, superior weather resistance and little need for growth regulators.

Merilou was originated from a hybridization made by the inventor in a controlled breeding program in Wateringen, The Netherlands in 1987. The female parent was an unnamed and proprietary Enthoven seedling, characterized by its compact growth. The male parent of Merilou was an unnamed and proprietary Enthoven seedling, characterized by its weather resistance.

Merilow was discovered and selected as one flowering plant within the progeny of the stated cross by Adrianus W. M. Enthoven in June 1988 in a controlled environment in Wateringen, The Netherlands.

The first act of asexual reproduction of Merilou was accomplished when vegetative cuttings were taken from the initial selection in August 1988 in a controlled environment in Wateringen, The Netherlands under the supervision of Adrianus W. M. Enthoven.

Horticultural examination of selected units initiated in the spring and summer of 1989 and continuing thereafter has demonstrated that the combination of characteristics as herein disclosed for Merilou are firmly fixed and are retained through successive generations of asexual reproduction.

Merilou has not been observed under all possible environmental conditions. The phenotype may vary with variations in environment such as temperature, light intensity and day length, without, however, any variation in genotype.

The following measurements, and comparisons describe plants grown in Wateringen, The Netherlands under greenhouse and outdoor conditions which approximate those generally used in commercial practice.

The following traits have been repeatedly observed and are determined to be basic characteristics of Merilou, which in combination, distinguish this geranium as a new and distant cultivar:

1. The plant has a compact growth habit and grows rather wide.
2. The foliage is green (RHS 138A) with a light zone on the upper side.
3. The leaf margins are slightly incised, double-crenated and very wavy.
4. The leaf stalk is green and sturdy.
5. The flower stalk is short and grows above the plant.
6. The inflorescence is large with many flowers that open at the same time.
7. The flowers are large in diameter.
8. The little flower stalks are long and bright red in color.
9. The flower buds are numerous and elliptic in shape.
10. The flowers are semi-double and pale lilac in color.
11. The lower flower petals have a pale lilac spot.
12. Flowering is average and is uniform.
13. Plants produce an inflorescence after each pair of foliage and each inflorescence flowers a long time.
14. Plant growth is so controlled that growth regulators are not needed.
15. Plants transport well because of their dark green foliage.

Of the many commercial cultivars known to the present inventor, the most similar in comparison to Merilou is the cultivar Burbanco (PEL 427). Reference is made to Chart A which compares certain characteristics of Merilou to those same characteristics of Burbanco. In general comparison to Burbanco, Merilou has, among other things, a strong undulation of the leaf blade margin and the flower has a white zone at the base of the upper petal.

The accompanying color photographic drawings show typical flower and foliage characteristics of Merilou, with colors being as true as possible with illustrations of this type.

Sheet 1 is a side view of Merilou grown in a 10.5 cm pot for approximately 8 weeks showing the foliage, flower stalks and inflorescences.

Sheet 2 is a close-up view of the upper and lower sides of a typical leaf from Merilou.

Sheet 3 is a close-up view of a typical flower from Merilou showing the flowers from the top and bottom.

In the following description color references are made to the Royal Horticultural Society Colour Chart (RHS) and Horticultural Colour Chart (HCC). The color values were determined between 2:10 and 2:30 p.m. on Jul. 31, 1989 under 21,500 Klux light intensity in Wateringen, The Netherlands.

Classification:

*Botanical.*—*A hybrid of the genus Pelargonium zonale* cv. Merilou.

*Commercial.*—Zonal geranium.

INFLORESCENCE

A. Umbel:

*Average diameter.*—Indoor, 122 mm.

*Average depth.*—Indoor, 90 mm.

*Peduncle length.*—Indoor, 172 mm.

*Pedicel length.*—Indoor, 35 mm.

*Pedicel color.*—Red to dark red at the top.

B. Corolla:

*Average diameter.*—Indoor, 55 mm.

*Form.*—Semi-double (7 to 9 petals).

*Color (general tonality at a distance of three meters)*-.—RHS 71D - 68A, HCC 628-628/1.

*Color (main body, upper surface).*—RHS 71D - 68A, HCC 628-628/1.

*Color (near margin upper face).*—RHS 71D - 68A, HCC 628-628/1.

*Color (lower side of petal).*—RHS 71D - 68A, HCC 628-628/1. Color dark spot center of upper face of petals is RHS 57B and spot is stronger on upper petals. White markings on upper face of upper petals at point of attachment. Color of veins on lower face of petals is 57B.

*Diameter lower petals.*—21 mm.

*Length lower petals.*—26 mm.

Diameter upper petals.—16 mm.

*Length upper petals.*—28 mm.

*Petal shape.*—Obovate.

*Sepal color.*—Green with red veins at bottom.

C. Bud:

*Shape.*—Elliptic.

*Color.*—Slightly lighter than corolla.

*Pedical.*—Red, to dark red at top.

D. Reproductive organs:

*Androecium.*—7–9 anthers.

*Gynoecium.*—4–5 stigma.

E. Spring flowering:

*Response period.*—In Wateringen, The Netherlands in 1989, 60% of plants with at least 1 open flower 13 weeks after planting unrooted cuttings.

F. Outdoor flower production: The flower count in 1989 in Wateringen, The Netherlands was between 41–46 flowers per plant from June through October observation period.

G. Durability: 100% shatter resistance.

PLANT

A. Foliage:

*Form.*—Kidney-shaped, with open base

*Margin.*—Bicrenate.

*Color.*—Green.

*Zonation.*—Light (RHS 137B).

*Length.*—39 mm.

*Diameter.*—67 mm.

B. General appearance and form:

*Internode length.*—30 mm.

*Branching pattern.*—an average of 4.3 branches per plant.

*Height.*—222 mm.

*Diameter.*—222 mm.

C. Tolerance to *Botrytis:* Good.

CHART A

COMPARISON OF MERILOU AND BURBANCO

| | Merilou | Burbanco |
|---|---|---|
| Leaf blade: Undulation of margin | strong | medium |
| Bud: Form | elliptic | narrow elliptic |
| Flower: Upper petal white zone at the base | present | absent |
| Flowering time: | average | early |

I claim:

1. A new and distinct cultivar of geranium plant named Merilou, as illustrated and described.

* * * * *

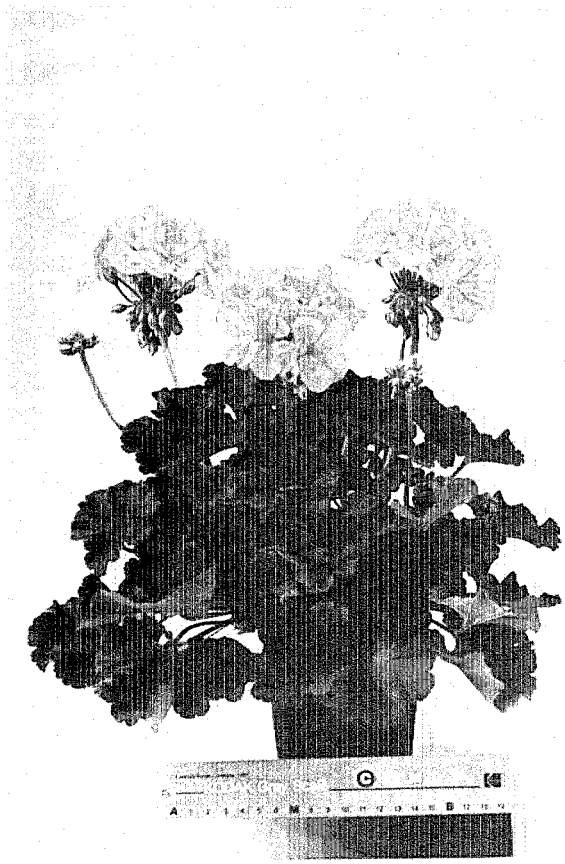

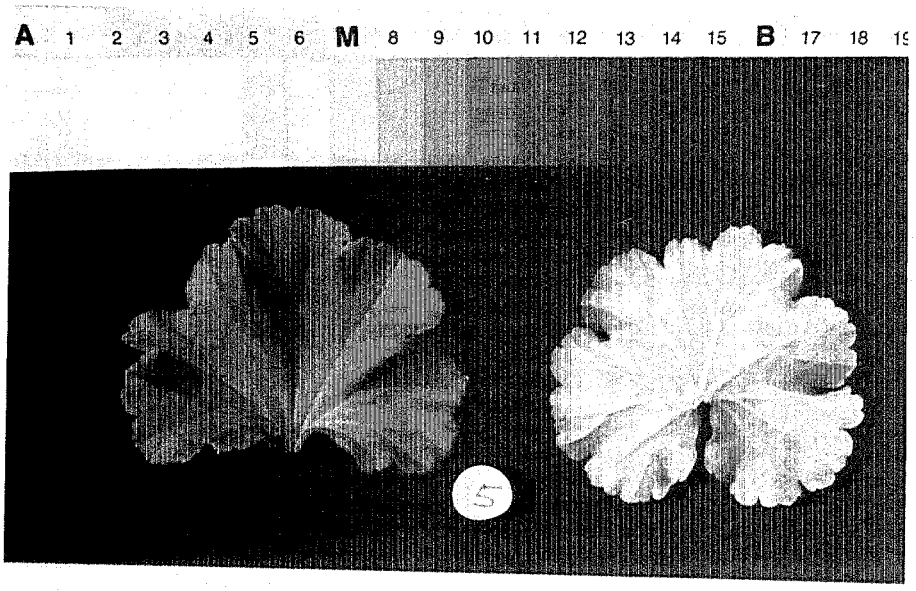
A 1 2 3 4 5 6 M 8 9 10 11 12 13 14 15 B 17 18 19
5

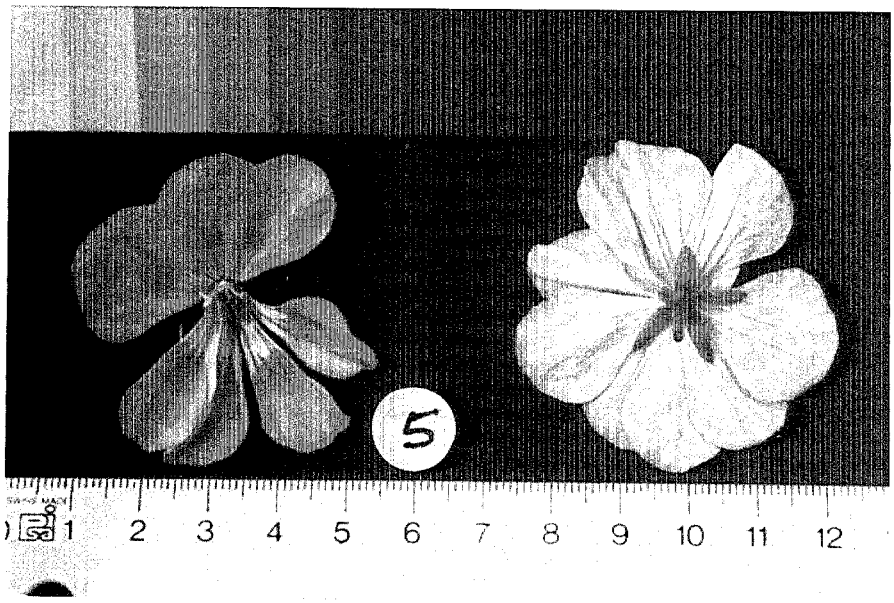
5
1 2 3 4 5 6 7 8 9 10 11 12